(12) United States Patent
Sage et al.

(10) Patent No.: US 7,678,337 B2
(45) Date of Patent: Mar. 16, 2010

(54) ASSEMBLY FOR CARRYING AND HOLDING SLIDES

(75) Inventors: Russell L. Sage, McHenry, IL (US); Robert W. Jaekel, Deer Park, IL (US)

(73) Assignee: Abbott Laboratories Inc., Abbott Park, IL (US)

( * ) Notice: Subject to any disclaimer, the term of this patent is extended or adjusted under 35 U.S.C. 154(b) by 1330 days.

(21) Appl. No.: 11/115,496

(22) Filed: Apr. 26, 2005

(65) Prior Publication Data

US 2006/0239868 A1    Oct. 26, 2006

(51) Int. Cl.
*B01L 9/00* (2006.01)
*G02B 21/26* (2006.01)

(52) U.S. Cl. .................. 422/104; 359/391; 356/244; 206/456; 206/560; 206/561; 206/562; 206/563; 206/564

(58) Field of Classification Search ............ 206/456, 206/557, 560–564; 359/391; 269/127–129; 356/244; 40/642.02
See application file for complete search history.

(56) References Cited

U.S. PATENT DOCUMENTS

| | | | |
|---|---|---|---|
| 4,274,359 A * | 6/1981 | Di Maggio et al. ............ | 118/56 |
| 4,651,671 A * | 3/1987 | Pedersen ................... | 118/57 |
| 5,439,649 A | 8/1995 | Tseung et al. | |
| 5,948,359 A | 9/1999 | Kalra et al. | |
| 7,403,330 B2 * | 7/2008 | Henderson et al. .......... | 359/391 |

OTHER PUBLICATIONS

BioGenex i6000 Automated Staining System, BioGenex, San Ramon, CA 94583, 2002.

* cited by examiner

*Primary Examiner*—Jill Warden
*Assistant Examiner*—Paul S Hyun
(74) *Attorney, Agent, or Firm*—David L. Weinstein

(57) ABSTRACT

A slide holder comprising a rectangular frame having two side walls facing each other, a first end wall facing a second end wall, the second end wall having a latch pivotally attached thereto, the latch capable of being pivoted in such a manner as to enable locking and unlocking of the slide holder in a slide holder carrier. The slide holder carrier has a first end wall, a first side wall, a second end wall, a second side wall, and a shaft running from the first end wall of the slide holder carrier to the second end wall of the slide holder carrier. At least one slide holder is rotatably mounted on the shaft.

4 Claims, 9 Drawing Sheets

ASSEMBLY FOR CARRYING AND HOLDING SLIDES

BACKGROUND OF THE INVENTION

1. Field of the Invention

This invention relates to systems that employ slides for mounting specimens to be examined under a microscope. The invention further relates to devices for handling such slides in such systems.

2. Discussion of the Art

High throughput automatic staining systems, such as the BioGenex i6000® Automated Staining System is used for in situ testing to provide accurate and reproducible staining results for better selection of therapy for patients. The BioGenex i6000® Automated Staining System has a capacity of 60 slides, i.e., five racks, with 12 slides per rack. U.S. Pat. Nos. 5,439,649 and 5,948,359 describe and illustrate embodiments of an automatic staining apparatus.

In a typical operation of the automatic staining system, a plurality of slides, each generally having a tissue sample at some location on its upper surface, are place horizontally in a tray that is inserted into the apparatus at a fixed location, usually at a location having registration pins that fit into registration holes in the tray (or similar registration elements) so that the individual microscope slides are always located in the same relative positions on the frame of the apparatus. The apparatus is programmed as appropriate for the individual slides being treated and reagents and reagent containers are placed at specified locations in the apparatus in the same manner as the tray previously described. Likewise reagent application tips are also made available for pickup by an automated mechanism. For example a standard box of 1-ml pipette tips can be placed at a specified location in the apparatus.

Once all the components are in place, the apparatus carries out all reagent applications, incubation, heating (if necessary or appropriate), and sample rinsing steps to perform the desired staining operation. In a typical operating sequence, a movable arm picks up a detachable wash/blow tip having a slit exit, and a buffer solution is applied to each of the sample slides being treated in a particular cycle by a liquid supply line and wash buffer reservoir attached via the supply line to the hollow tip head. The apparatus ten uses the same wash/blow tip to blow excess buffer off the slide prior to reagent delivery. This is accomplished by blowing air through the tip while the head travels down the length of the slide; a "wall" of air exits the slit and removes excess buffer from the slid without disrupting the tissue sample. A small amount of buffer is left on the slide to assist in reagent spreading. The wash/blow tip is then returned to its holder by the automated arm.

The arm then picks up a disposable pipette tip from the pipette tip box that has been inserted in to the reagent application tip holder in the apparatus. The arm with the pipette tip attached picks up a reagent to be applied to the slide or group of slides from a reagent vial. A number of the slides can be treated at the same time. The reagent is dispensed on the slide in a preassigned pattern that works in combination with the thin liquid film on the microscope slide to assure spreading of the reagent over the entire surface of the slide to which the tissue may be attached. The thin liquid film allows less reagent to be used than would be require if the film were not present to assist reagent spreading.

The disposable pipette tip is then discarded, and the movable arm picks up the wash/blow tip for adding buffer to and then blowing excess buffer off the next group of slides to be processed which the rest group of slide are being incubated with the reagent, after which the wash/blow tip is returned to its holder. The arm picks up the next available from the tip box, and reagent is drawn in to the tip and applied as before. Appropriate steps are repeated until all slides have been treated with reagent or until a reagent incubation is complete so that reagents must be removed from appropriate slides.

Once a reagent incubation is complete, slides are rinsed when the movable arm picks up the wash/blow tip again and buffer is applied to the slide to rinse off the majority of the reagent. The wash/blow head then blows the excess buffer from the slide, and the slide is rinsed a second time with the on-line buffer, if necessary. This procedure of rinsing a drying a slide is repeated as necessary depending upon the individual stain and the appropriate procedure for rinsing the reagent.

Although many staining operations can be carried out without heating the slides, some staining techniques can be enhanced by providing heat so that either incubation or drying times are shortened, thereby increasing the speed of the overall operation. FIG. 8 of U.S. Pat. No. 5,439,649 six views of a tray 190 intended to hold ten (10) standard 1-inch×3-inch microscope slides. Tray 190 is formed into a series of individual wells 192 for microscope slides; the location of a single microscope slide 130 is shown by a dotted line in the right-most well of the plan view of FIG. 8. The bottom of the individual wells is open. The opening allows the surface of a heating element to directly contact the bottom of each microscope slide.

Improvements in the trays shown in U.S. Pat. No. 5,948,359 have been and are continuing to be made. According to U.S. Pat. No. 5,948,359, especially FIGS. 13A-13E, devices designated as trays 190 are used to hold microscope slides 130. The tray 190 is formed into a series of individual wells 192 for microscope slides. Individual side walls 194 separate each well from 192 from its adjacent wells to prevent accidental contact of liquid, such as might occur during a washing operation, and to prevent contamination between adjacent microscope slides. The side walls 194, retaining tabs 196, and bracing feet 197 closely and accurately retain microscope slides placed in the individual wells. A gap 198 is present at one end of the well 192 to allow easy grasping of an individual microscope slide 130 between thumb and forefinger for insertion into and removal from the tray 190.

The trays in use today are typically made of stainless steel sheet metal and have metal retaining tabs. When the microscope slide is inserted in or removed from the tray, by moving the microscope slide under the retaining tabs, the cover slip of the microscope slide is sometimes snagged by the retaining tabs, and, consequently, the cover slip is moved out of place on the microscope slide by the retaining tabs. The cover slip is a small sheet of glass, typically between 18 and 25 mm on a side. The cover slip serves at least two purposes: (1) it protects the objective lens of the microscope from contacting the specimen, and (2) it creates an even thickness (in wet mounts) for viewing. The microscope slide may not easily fit under the retaining tabs that are formed into the tray, with the result that the microscope slide must be pulled carefully so that the retaining tabs are avoided or pushed carefully so that the retaining tabs are avoided. Designs for trays used at this time have need for improvement in several areas.

In addition, the latch or other device that releases the microscope slide from the tray is not easily accessible by the operator. The operator's fingers frequently contact the waste material tray, which is located at the base of the instrument where the heaters are mounted, as the tray is being released from the apparatus. The tray may not allow the microscope slide to rest flat on the surface of the heater when the tray is positioned on the instrument. Furthermore, the microscope slide cannot be easily removed from the tray during the course of a run, because it must be slid under the retaining tabs. Still further, the suction from the automated cover slip remover could cause the latch to open, thereby releasing the slide holder from the latched position during the run.

Because of the foregoing problems, it is desired to provide a tray, or slide holder, that is easily accessible to the operator before, during, and after a run. It is also desired that the tray, or slide holder, be easy to load with a microscope slide. It tray, or slide holder.

SUMMARY OF THE INVENTION

In one aspect, this invention provides a slide holder comprising a rectangular frame having two side walls facing each other, a first end wall facing a second end wall, the second end wall having a latch rotatably attached thereto, the latch capable of being pivoted about the second end wall to lock the slide holder to a slide holder carrier or to unlock the slide holder from the slide holder carrier. Each of the side walls has a first end abutting the first end wall of the frame and a second end abutting the second end wall of the frame. The first end of each side wall has an opening through which a shaft is placed. The ends of the shaft are affixed to the slide holder carrier, and the slide holder can be caused to rotate about the shaft to facilitate access of the slide holder to a mechanism for placing a slide onto the slide holder or removing a slide form the slide holder. Proximate to the first end of each side wall of the rectangular frame or proximate to the second end of each side wall of the rectangular frame or proximate to both ends of each side wall of the rectangular frame can be located positioning guides to aid in placing a slide into the proper position on the slide holder.

Each of the side walls of the rectangular frame can have a recessed area, whereby the elongated edges of a standard glass microscope slide positioned in the slide holder are sufficiently exposed that the slide can be gripped by a mechanism capable of lifting a slide from the slide holder or placing a slide onto the slide holder. Examples of such a mechanism include, but are not limited to, the thumb and a finger, or a robotic mechanism. Each of the side walls of the rectangular frame has an opening proximate the second end thereof to enable a pivot pin of the latch to be placed into the side wall.

The first end wall comprises a back surface, a front surface, a horizontal platform extending between the back surface and the front surface, a first side surface that abuts one side wall of the frame, and a second side surface that abuts the other side wall of the frame. Projecting upwardly from the horizontal platform is a retaining element, which serves the function of preventing movement of a slide in a direction away from the second end wall.

The second end wall comprises a back wall, a front surface, a horizontal platform extending between the back surface and the front surface, a first side surface that abuts one side wall of the frame, and a second side surface that abuts the other side wall of the frame. The horizontal platform of the second end wall can have a recessed area to enable a slide to be grasped by a mechanism capable of lifting a slide from the slide holder or placing a slide onto the slide holder. Examples of such a mechanism include, but are not limited to, the thumb and a finger, or a robotic mechanism. Thus, a slide positioned in the slide holder can be grasped at the edges of the slide or at one end of the slide to enable the slide to be removed easily from the slide holder by the finger and thumb of the operator or by a mechanism that performs the same function as the finger and thumb of the operator without touching a major portion of the surface of the slide.

The latch rotatably attached to the second end wall comprises:

(a) a first leg having a first end and a second end;
(b) a second leg having a first end and a second end;
(c) the first end of the first leg having an element projecting therefrom, the projecting element capable of fitting into an opening in the side wall of the frame adjacent to the first end of the first leg;
(d) the first end of the second leg having an element projecting therefrom, the projecting element capable of fitting into an opening in the side wall of the frame adjacent to the first end of the second leg;
(e) a third member disposed between the first leg and the second leg, the third member having a projecting element disposed between the first end of the first leg and the second end of the first leg and the first end of the second leg and the second end of the second leg, the projecting element projecting from a surface of the third member, whereby the projecting element of the third member is capable of engaging a notch in the slide holder carrier in order to lock the slide holder to the slide holder carrier;
(f) a projecting element on the first leg on the side opposite to that of the projecting element of component (e) to hold down a slide; and
(g) a projecting element on the second leg on the side opposite to that of the projecting element of component (e) to hold down a slide.

In another aspect, this invention provides an assembly comprising the slide holder previously described and a slide holder carrier having a first end wall, a first side wall, a second end wall, and a second side wall. A shaft runs from the first end wall of the slide holder carrier to the second end wall of the slide holder carrier. At least one slide holder is rotatably mounted on the shaft. The slide holder carrier can further include a plurality of ribs that divide the slide holder carrier into a plurality of cells, the ribs running from the first side wall of the slide holder carrier to the second side wall of the slide holder carrier. In each cell, a side wall of the slide holder carrier can have a notch formed therein for mating with the projecting element of the latch to lock the slide holder to the slide holder carrier.

The invention allows a microscope slide to be inserted into and removed from the slide holder easily. The slide holder includes a latch that will prevent the slide holder from moving excessively during the process of removing a cover slip from the slide. When the latch is unlocked to enable insertion or removal of the slide, the projecting elements that hold down the slide are moved away from the major surface of the slide itself and the surface of the slide holder supporting the slide for ease of loading and unloading the slide, thereby allowing the slide to be removed from the slide holder without inadvertently removing the cover slip. The latch also has a built-in stop to prevent the latch from rotating completely around and allowing the slide holder to fall through the slide holder carrier when not in use. The locking feature of the latch of the slide holder accurately positions the slide holder in the slide holder carrier, thereby allowing the slide to float, thereby further ensuring that the major surface of the slide not bearing the specimen can be caused to come into contact with the surface of a heater when the specimen is required to be heated. The feature for allowing a slide to be removed from the slide holder via vertical lifting, in place of the horizontal sliding feature for removing a slide from a conventional slide holder, eliminates the situation in which the retaining tabs of the conventional slide holder peel the cover slip from the major surface of the slide.

DETAILED DESCRIPTION

As used herein, the phrase "slide holder" means a device by which slides suitable for use with a microscope are held during operation of an apparatus wherein the samples on the slides are treated for further analysis. The phrase "slide holder carrier" means a device to which the slide holder is attached. The slide holder carrier is also the device that is inserted into the apparatus wherein the samples on the slides are treated for further analysis. The phrase "mechanism of lifting the slide" includes, but is not limited to, such mechanisms as human mechanisms, e.g., the thumb and forefinger, automated mechanisms, such as robotic devices that have a gripping feature. The term "slide" is intended to include a small glass plate for mounting biological specimens to be examined under a microscope.

Figure 1:
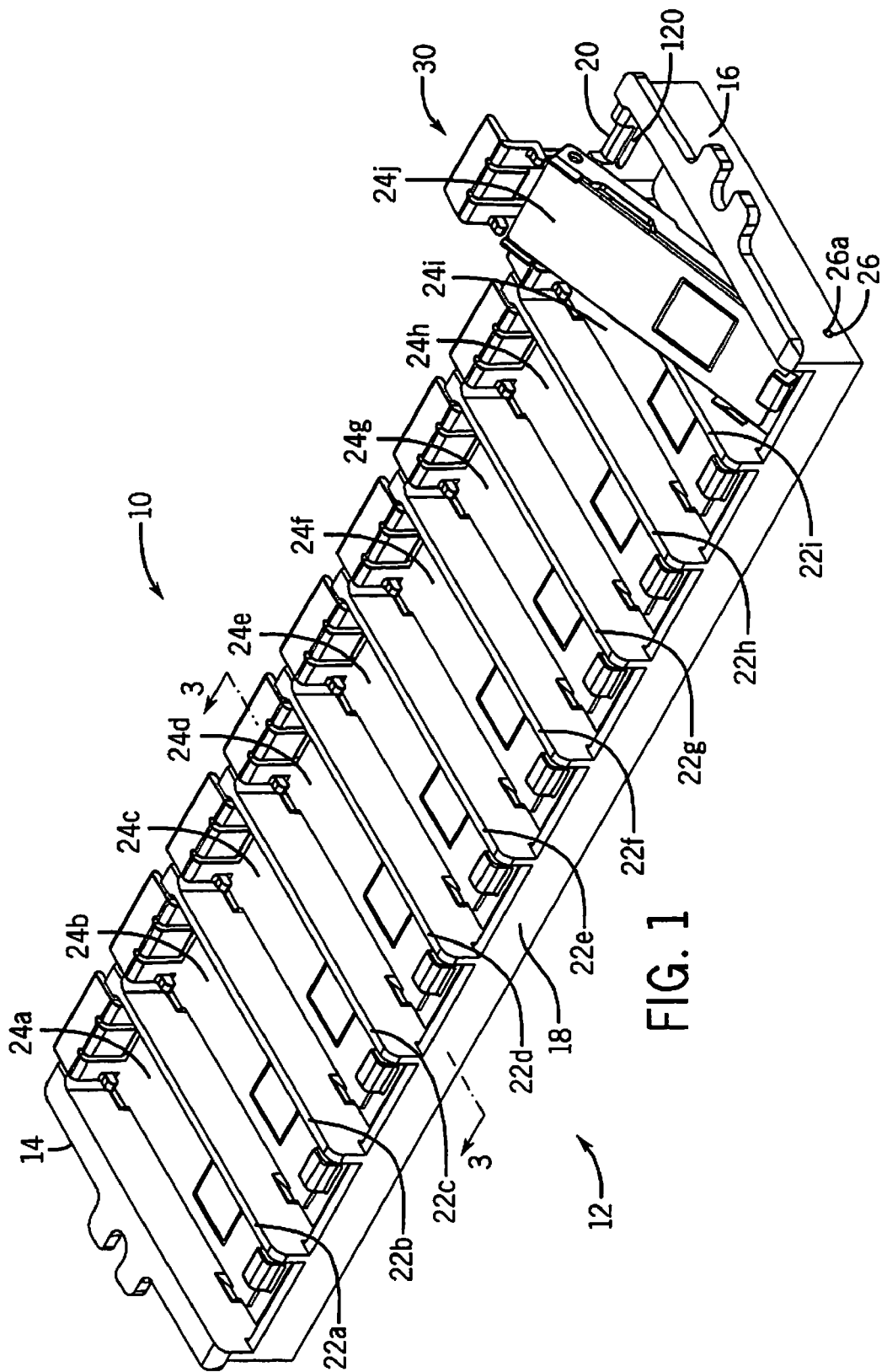
FIG. 1 is a perspective view of an assembly in which a slide holder carrier of this invention contains a plurality of slide holders of this invention, each slide holder supporting a slide. In this view, the latches of nine of the slide holders are in the locked position, and the latch of one of the slide holders is in the unlocked position.
Figure 2:
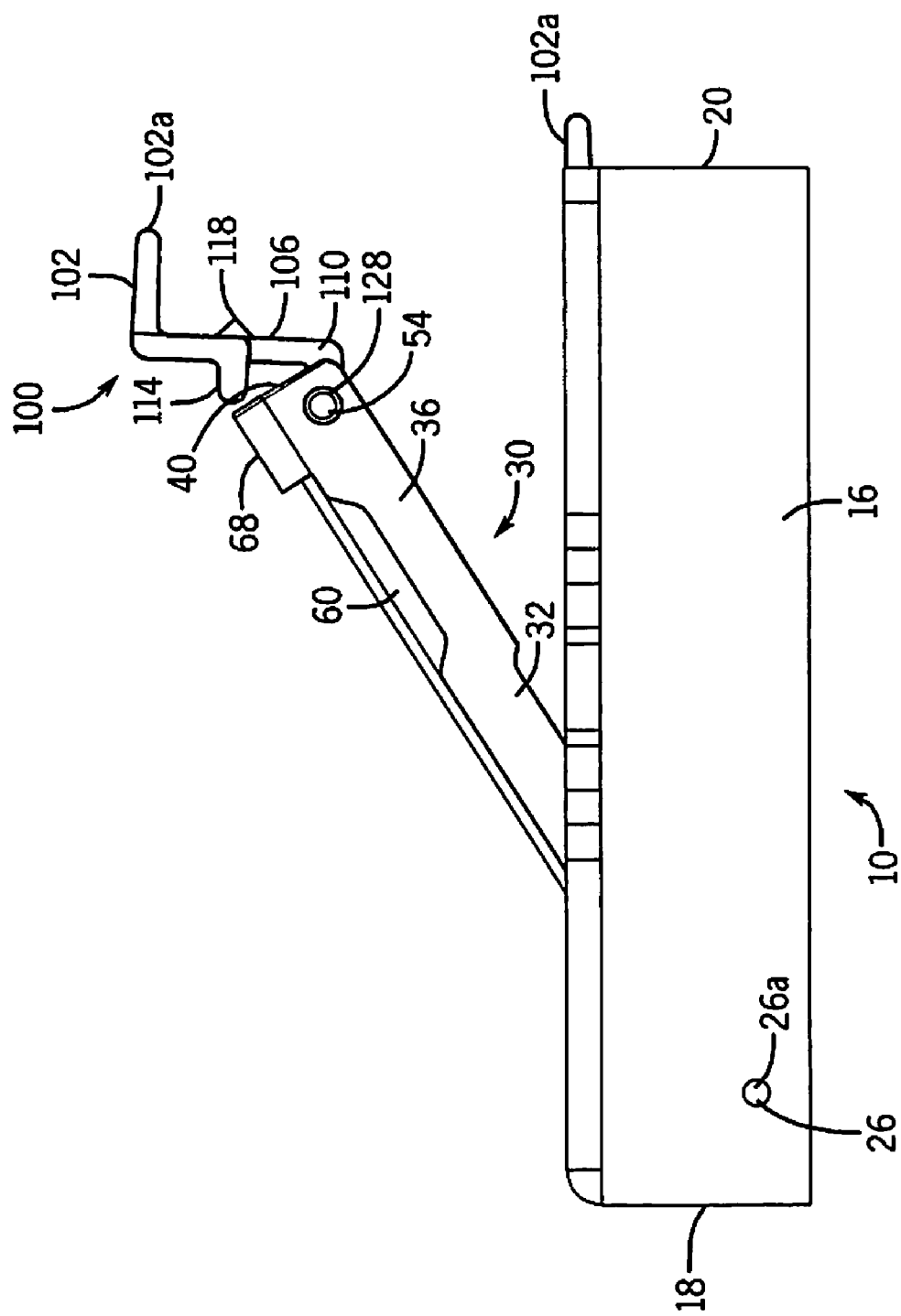
FIG. 2 is a side view in elevation of the assembly of FIG. 1. In this view, a slide holder is shown in the unlocked position and rotated upward about 45° from the horizontal.
Figure 3:
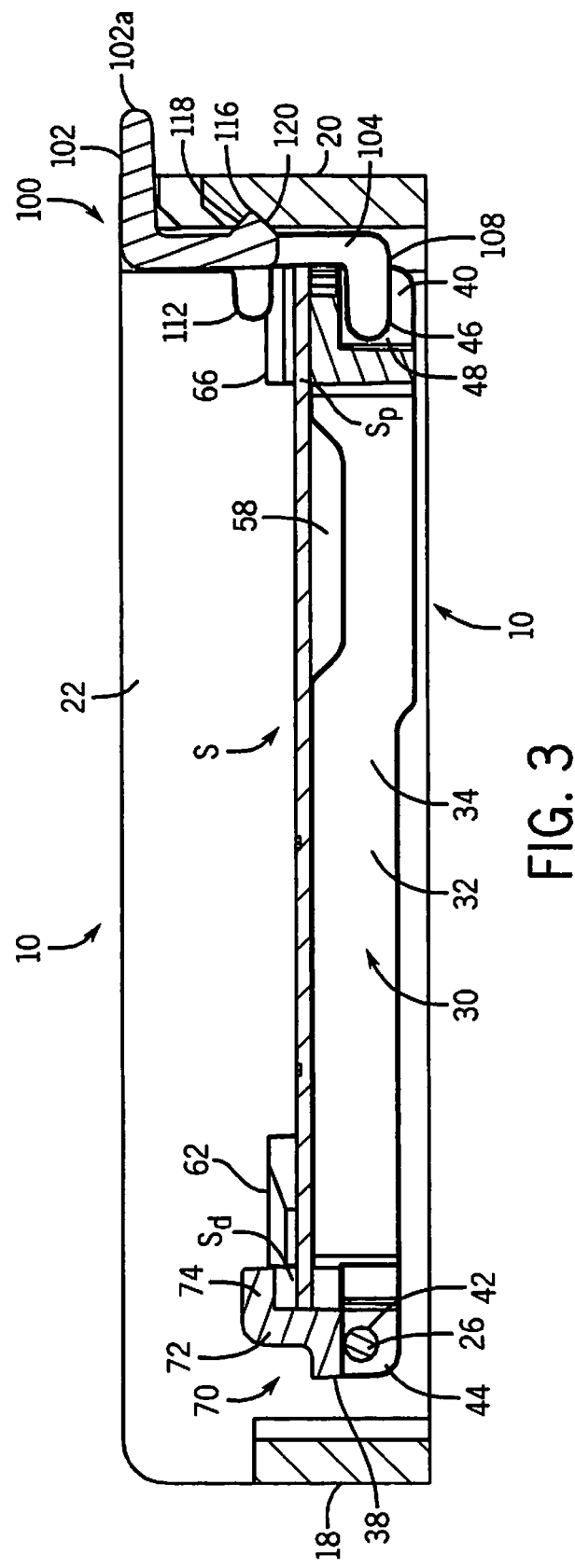
FIG. 3 is a sectional view of the assembly of FIG. 1 taken along line 3-3. The latch of the slide holder is shown the locked position.
Figure 4:
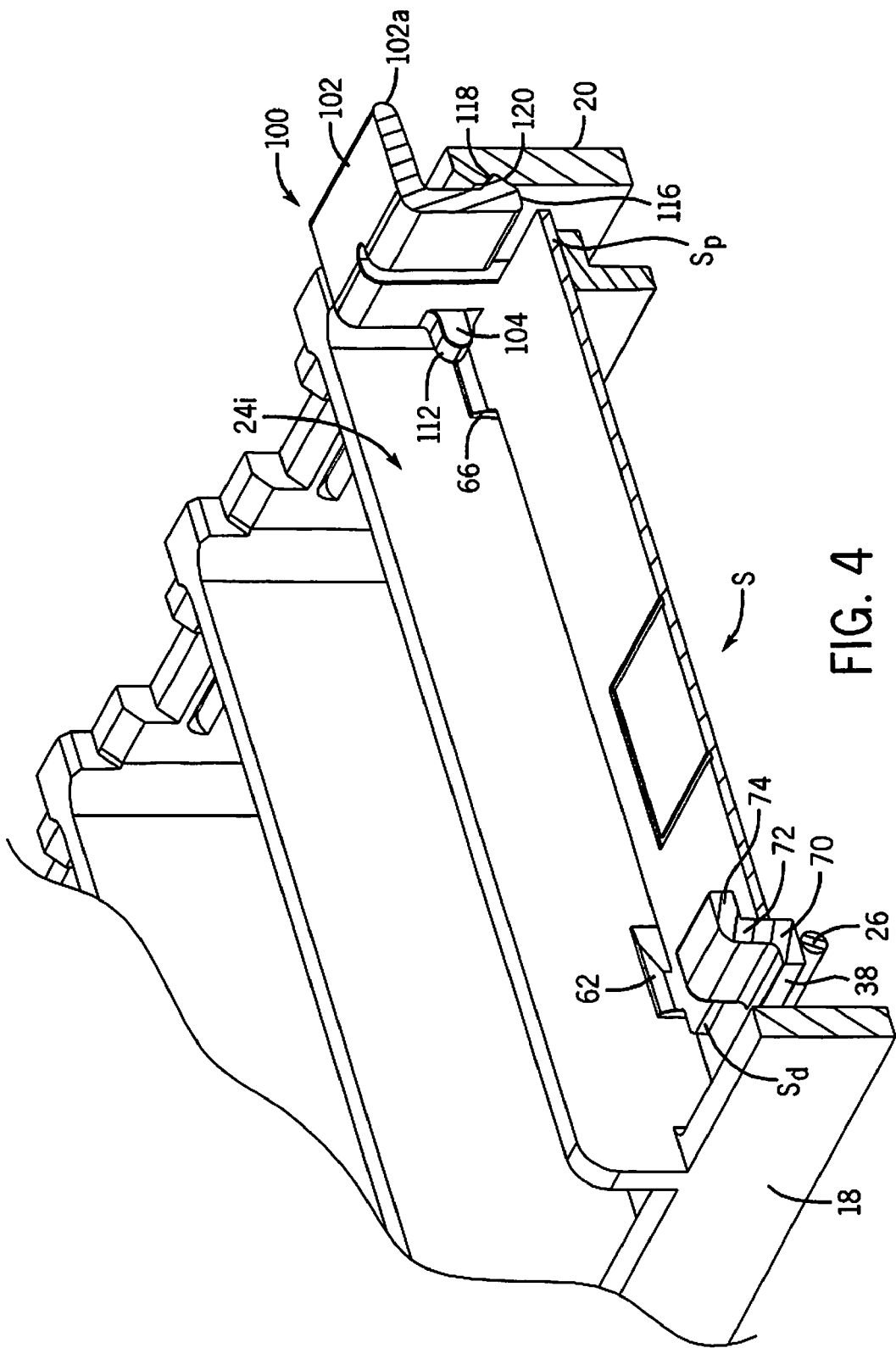
FIG. 4 is a perspective view of the sectional view of the assembly as shown in FIG. 3. The latch of the slide holder is shown the locked position.
Figure 5:
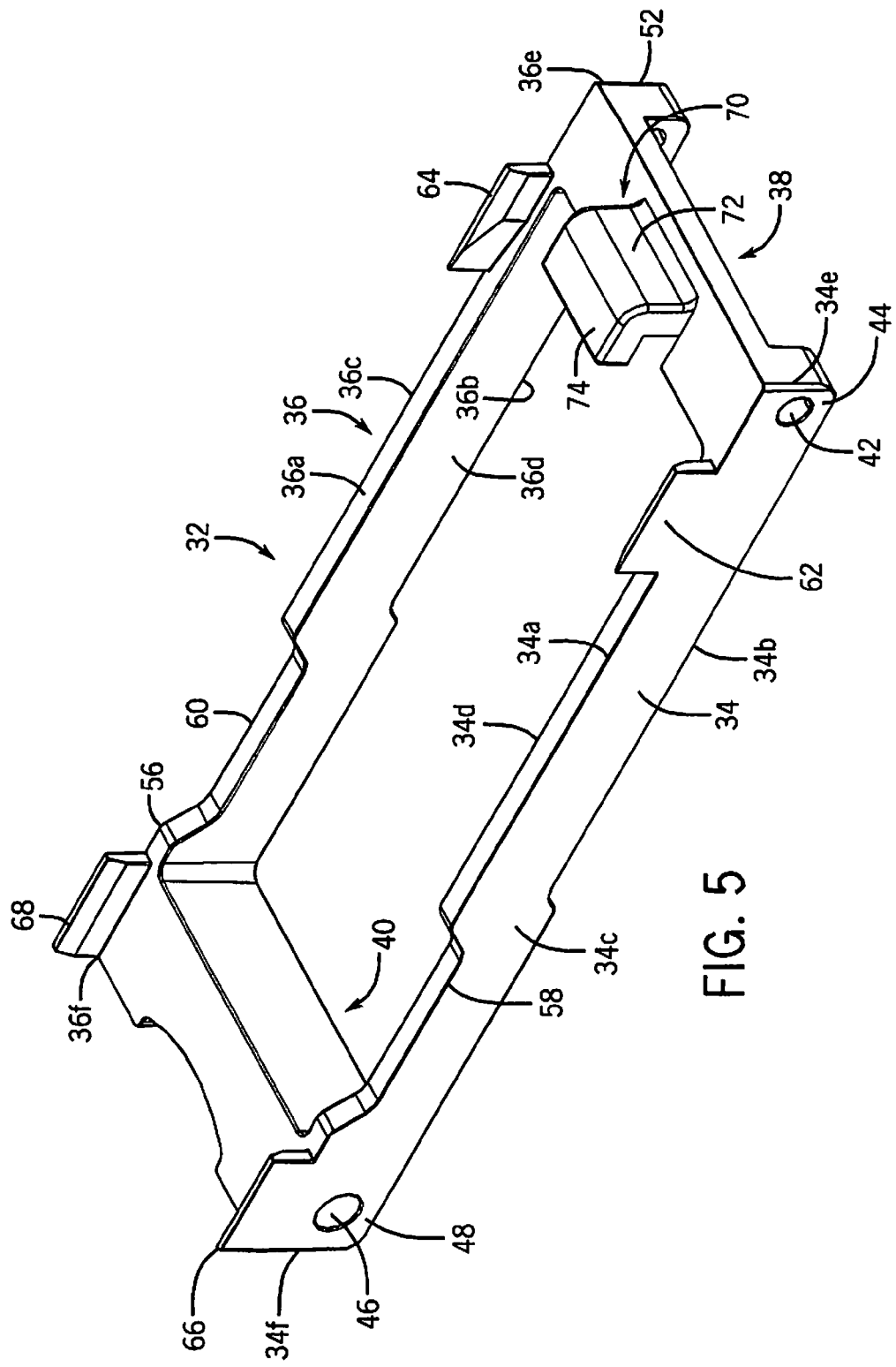
FIG. 5 is a perspective view of the frame of the slide holder shown in FIG. 1.
Figure 6:
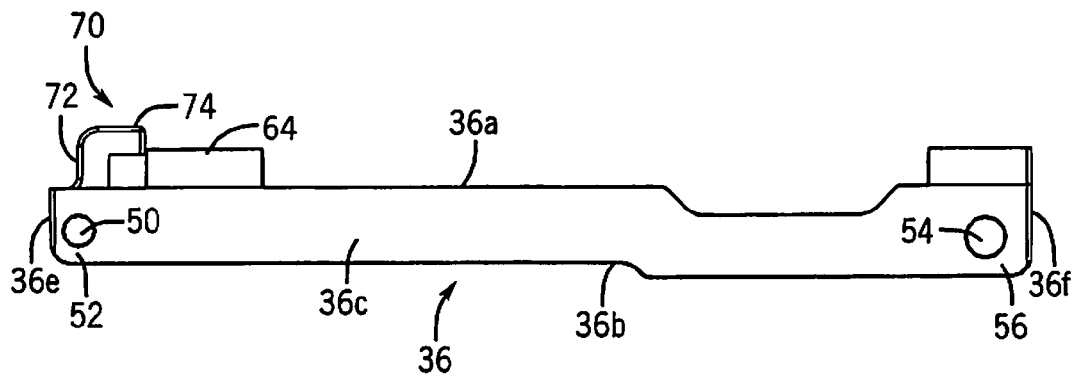
FIG. 6 is a side view in elevation of the frame of the slide holder shown in FIG. 5.

Referring now to FIGS. 1, 2, 3, and 4, a slide holder carrier 10 comprises a rectangular frame 12 comprising two end walls 14,16 and two side walls 18, 20. The frame 12 has a plurality of ribs 22a, 22b, 22c, 22d, 22e, 22f, 22g, 22h, and 22i, which divide the frame into a plurality of cells 24a, 24b, 24c, 24d, 24e, 24f, 24g, 24h, 24i, and 24j. As shown in FIG. 1, the slide holder carrier 10 comprises ten cells. Each cell 24a, 24b, 24c, 24d, 24e, 24f, 24g, 24h, 24i, and 24j is of sufficient size to accommodate a slide holder 30 of this invention. The slide holder carrier 10 includes an elongated shaft 26 having a first end and a second end. One end of the shaft 26 is attached to the first end wall 14 of the slide holder carrier 10, and the other end 26a of the shaft 26 is attached to the second end wall 16 of the slide holder carrier 10. The shaft 26 runs from the first end wall 14 of the slide holder carrier 10 to the second end wall 16 of the slide holder carrier 10. The shaft also runs through an opening formed through each rib 22a, 22b, 22c, 22d, 22e, 22f, 22g, 22h, and 22i. A plurality of slide holders 30 of this invention is supported by the shaft 26. The slide holders 30 are also capable of pivoting about the shaft 26. The slide holder 30 of this invention is designed to pivot about the shaft 26, in order to render the slide supported by the slide holder 30 accessible to a mechanism that is capable of introducing a slide into the slide holder 30 and removing a slide from the slide holder 30.

Referring also now to FIGS. 5, 6, 7, 8, and 9, the slide holder 30 has a rectangular frame 32 having two side walls 34 and 36, a first end wall 38 at one end of the rectangular frame 32, and a second end wall 40 at the other end of the rectangular frame 32. The side wall 34 has a top edge 34a, a bottom edge 34b, a first side face 34c, a second side face 34d, a first end edge 34e, and a second end edge 34f. The side wall 36 has a top edge 36a, a bottom edge 36b, a first side face 36c, a second side face 36d, a first end edge 36e, and a second end edge 36f.

Referring further now to FIGS. 5, 6, 7, 8, and 9, the side wall 34 has a first opening 42 formed in a first end 44 thereof and a second opening 46 formed in a second end 48 thereof. The side wall 36 has a first opening 50 formed in a first end 52 thereof and a second opening 54 (see FIG. 2) formed in a second end 56 thereof. The first opening 42 in the side wall 34 is in register with the first opening 50 in the side wall 36. The shaft 26 passes through the first openings 42 and 50. The second opening 46 in the side wall 34 is in register with the second opening 54 in the side wall 36. Projecting elements on the first ends of the legs of the latch, which will be described in detail below, are inserted into the second openings 46 and 54. The side wall 34 has a recessed area 58 formed in the upper edge 34a. The side wall 36 has a recessed area 60 formed in the upper edge 36a. The recessed area 58 is shown as being in register with the recessed area 60. The purpose of the recessed areas 58 and 60 is to provide adequate space to enable a slide to be grasped by a slide loading mechanism and a slide removal mechanism (e.g., a thumb and a finger of a human operator or an alternate mechanism, e.g., a robotic mechanism, an automated robotic mechanism). The side wall 34 has a first projection 62. The side wall 36 has a first projection 64. The first projection 62 is in register with the first projection 64. The purpose of the projections 62 and 64 is to promote proper positioning of the slide in the slide holder 30, thereby functioning as positioning guides. The side wall 34 has a second projection 66. The side wall 36 has a second projection 68. The first projection 62 is in register with the first projection 64. The second projection 66 is in register with the second projection 68. The purpose of the projections 66 and 68 is to promote proper positioning of the slide in the slide holder 30, thereby functioning as positioning guides.

In certain embodiments of this invention, the depth of the frame 32 (i.e., the width of a side face of a side wall) must be sufficiently low that the slide holder 30 does not interfere with the heating elements that are placed below the slide holders 30 and within the cells 24a, 24b, 24c, 24d, 24e, 24f, 24g, 24h, 24i, and 24j of the slide holder carrier 10. During heating of the specimens by the heating elements, the major surface of the slide not bearing the specimen is in contact with the heating element.

As shown in FIGS. 1, 2, 3, 5, and 6, the frame 32 is not in the form of a true parallelepiped. This departure from the form of a true parallelepiped results from the formation of the recessed areas 58 and 60 in the side walls 34 and 36, respectively of the frame 32. However, it is generally desired to have the width of each side face of each side wall be substantially unvarying along the length of each side face of each side wall because a substantially unvarying width for each side face of each side wall results in greater strength for the side walls. Furthermore, if the frame 32 is formed by means of a molding process, sidewalls having side faces of unvarying width enable simplification of the molding process.

Figure 7:
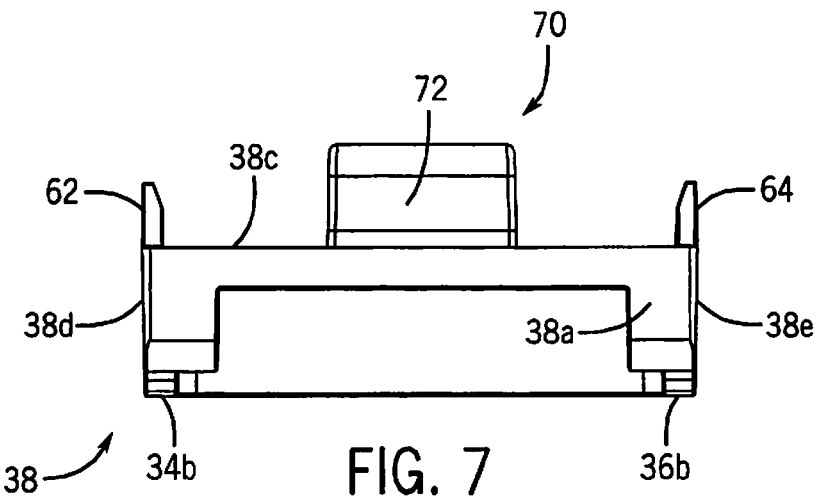
FIG. 7 is an end view in elevation of the first end wall of the frame of the slide holder shown in FIG. 5.
Figure 8:
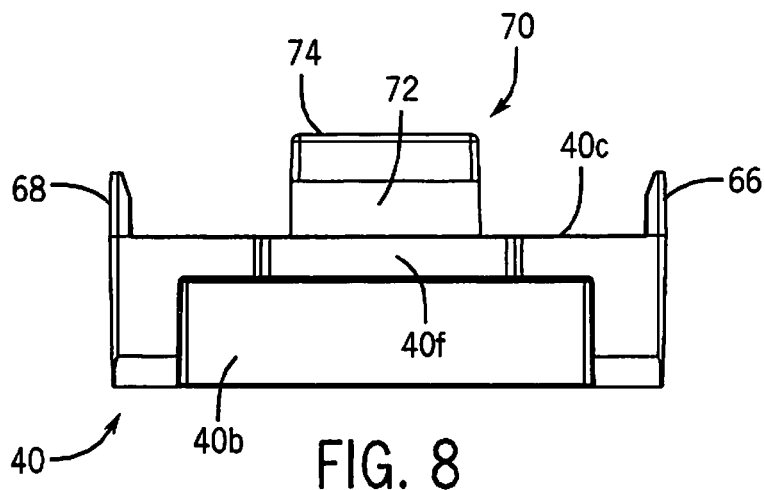
FIG. 8 is an end view in elevation of the second end wall of the frame of the slide holder shown in FIG. 5.
Figure 9:
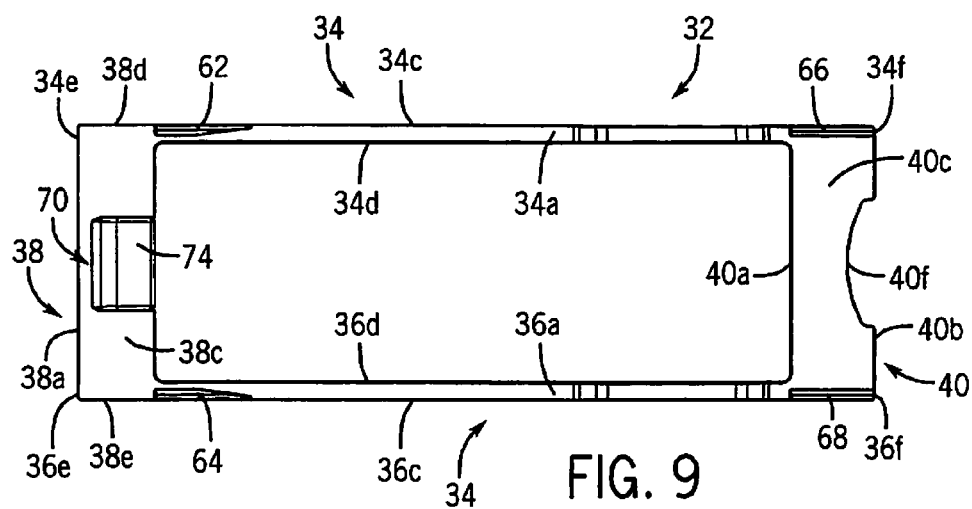
FIG. 9 is a top plan view of the frame of the slide holder shown in FIG. 5.
Figure 10:
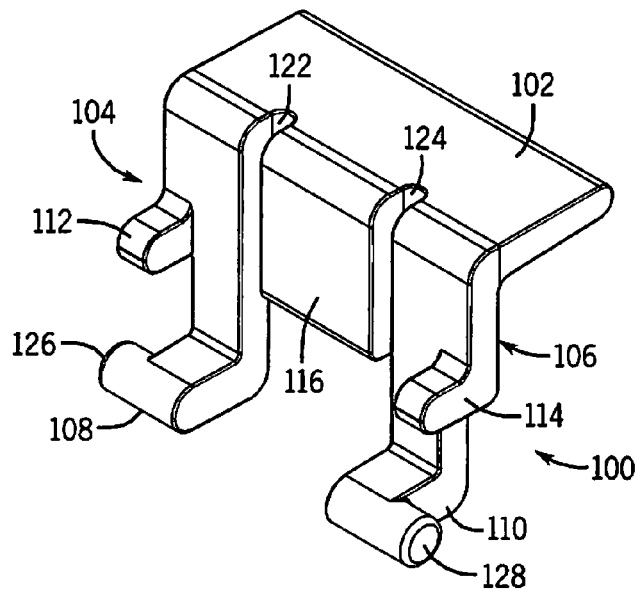
FIG. 10 is a perspective view of the latch of the slide holder shown in FIG. 1.
Figure 11:
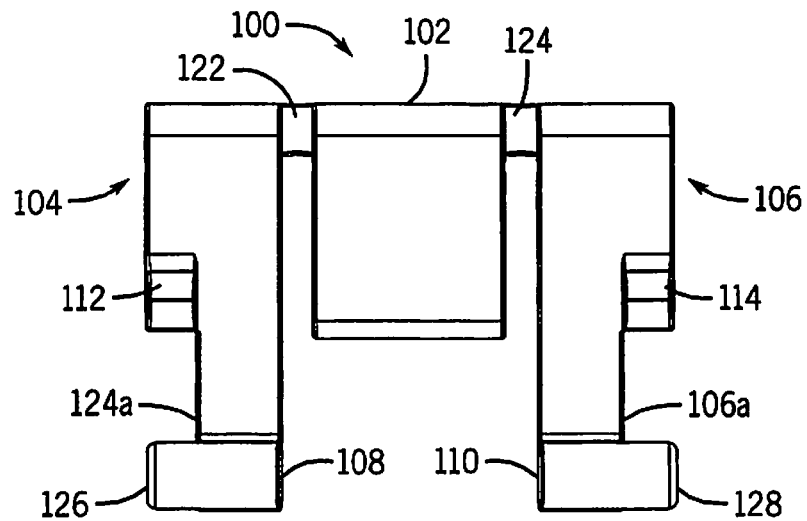
FIG. 11 is an end view in elevation of one end of the latch of the slide holder shown in FIG. 10.
Figure 12:
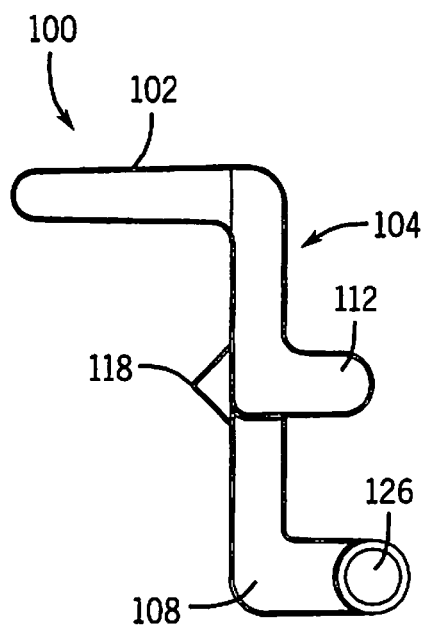
FIG. 12 is a side view in elevation of one side of the latch of the slide holder shown in FIG. 10.
Figure 13:
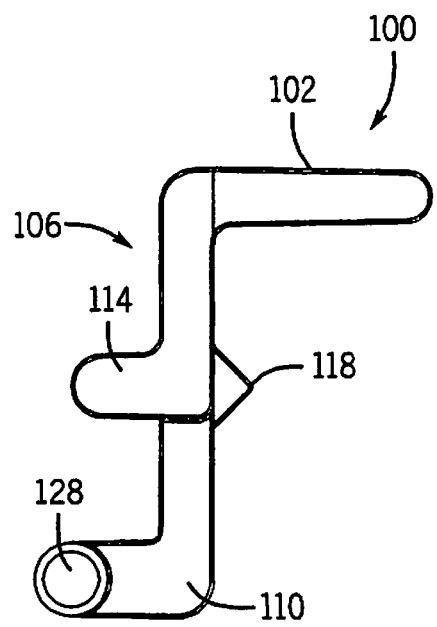
FIG. 13 is a side view in elevation of a side of the latch of the slide holder shown in FIG. 10, but not shown in FIG. 12.
Figure 14:
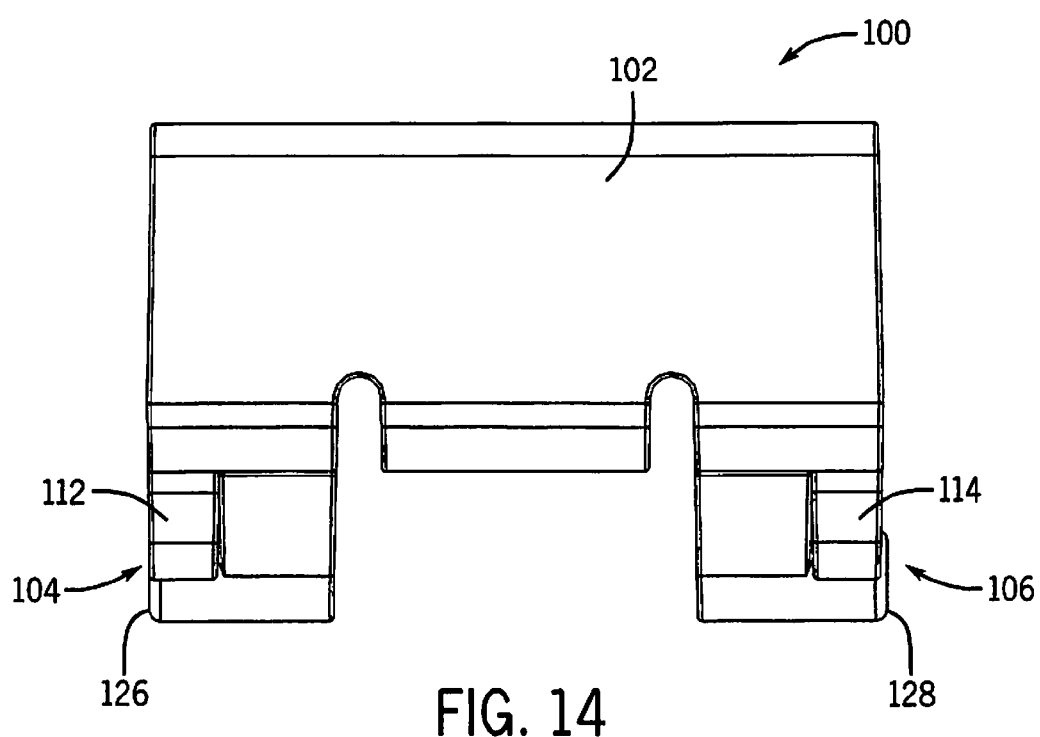
FIG. 14 is a top plan view of the latch of the slide holder shown in FIG. 10.

Referring now to FIGS. 7 and 9, the first end wall 38 comprises a back surface 38a, a front surface 38b, a horizontal platform 38c extending between the back surface 38a and the front surface 38b, a side surface 38d that abuts the side wall 34 of the frame 32, and a side surface 38e that abuts the side wall 36 of the frame 32. Projecting upwardly from the horizontal platform 38c is a retaining element 70, which serves the function of preventing movement of a slide in a direction away from the second end wall 40. As shown in FIGS. 6, 7, 8, and 9, the retaining element 70 comprises a vertical portion 72 having an overhanging portion 74, which projects from the uppermost end of the vertical portion 72. The vertical portion 72 prevents a slide positioned on the slide holder 30 from moving in a direction away from the second end wall 40. The overhanging portion 74 prevents a slide positioned on the slide holder 30 from moving excessively in a vertical direction when a force that would move the slide in a vertical direction, e.g., suction for removing a cover slip, is applied to the slide. However, a slight amount of vertical movement is not precluded.

When a slide is properly positioned in a slide holder 30, one end of the slide rests upon the upper surface of the horizontal platform 38c of the first end wall 38. The overhanging portion 74 of the retaining element 70 is sufficiently short to avoid catching or snagging of the slide when the slide is inserted into the slide holder 30 by a slide loading mechanism or removed from the slide holder 30 by a slide removal mechanism. The overhanging portion 74 of the retaining element 70 is also sufficiently resilient to prevent catching or snagging of the slide when the slide is inserted into the slide holder 30 by a slide loading mechanism or removed from the slide holder 30 by a slide removal mechanism.

Referring now to FIGS. 8 and 9, the second end wall 40 comprises a back surface 40a, a front surface 40b, a horizontal platform 40c extending between the back surface 40a and the front surface 40b, a side surface 40d that abuts the side wall 34 of the frame 32, and a side surface 40e that abuts the side wall 36 of the frame 32. It is preferred that a recessed area 40f be formed in the horizontal platform 40c to provide adequate space to enable the end of a slide to be grasped by a slide loading mechanism and a slide removal mechanism (e.g., a finger and a thumb of a human operator or an alternate mechanism, e.g., a robotic mechanism, an automated robotic mechanism).

Referring now to FIGS. 2, 3, 4, 10, 11, 12, 13, and 14, the latch 100 comprises a horizontal platform 102 from which projects a first leg 104 and a second leg 106. At one end 104a of the first leg 104 is a foot 108. At one end 106a of the second leg 106 is a foot 110. On the leg 104 between the horizontal platform 102 and the foot 108 is a projecting element 112. Likewise, on the leg 106 between the horizontal platform 102 and the foot 110 is a projecting element 114. The projecting elements 112 and 114 perform the function of securing or holding down an end of a slide when the latch 100 is in the locked position. The projecting elements 112 and 114 prevent a slide positioned on the slide holder 30 from moving excessively in a vertical direction when a force that would move the slide in a vertical direction, e.g., suction for removing a cover slip, is applied to the slide. However, a slight amount of vertical movement is not precluded. The latch 100 also has a member 116 located intermediate the first leg 104 and the second leg 106 and depending from the horizontal platform 102. The member 116 has a projecting element 118, which is capable of fitting into a notch 120 in the side of the side wall 20 of the slide holder carrier 10 facing the latch 100 when the latch 100 is in the locked position.

The member 116 is separated from the first leg 104 by a gap 122 and from the second leg 106 by a gap 124. The gaps 122 and 124 serve to enable the member 116 to be flexed in order that the projecting element 118 can be placed in the notch 120 in the side of the side wall 20 of the slide holder carrier 10 facing the latch 100. The material of which the latch is constructed is preferably sufficiently flexible and resilient to enable the member 116 to bend sufficiently so that (a) the projecting element 118 can engage the notch 120 when locking of the slide holder 30 to the slide holder carrier 10 is desired and that (b) the projecting element 118 can be disengaged from the notch 120 when unlocking of the slide holder 30 from the slide holder carrier 10 is desired. From the foot 108 projects a pin 126 to be inserted into the opening 46 in the side wall 34 of the frame 32. From the foot 110 projects a pin 128 to be inserted in the opening 54 in the side wall 36 of the frame 32. The pins 126 and 128 enable the latch 100 to pivot in such a manner so as to enable the latch 100 to move between the locked position and the unlocked position. The latch 100 can be caused to pivot about the axis running through the openings 46 and 54 by lifting the latch by the overhanging portion 102a of the horizontal platform 102 of the latch 100 or by lowering the latch by the overhanging portion 102a of the horizontal platform 102 of the latch 100. Lifting and lowering of the overhanging portion 102a of the horizontal platform 102 of the latch can be carried out by a human operator (e.g., a thumb and a finger of a human operator) or by an alternate mechanism (e.g., a robotic mechanism, an automated robotic mechanism). The overhanging portion 102a rests on the top of the side wall 20 of the slide holder carrier 10 when the latch 100 is in the locked position.

The frame 32 and the latch 100 can be made from a polymeric material, preferably a molded polymeric material. A representative example of a polymeric material suitable for preparing the frame 32 and the latch 100 is molded polycarbonate. Other polymeric materials having molding and resiliency characteristics substantially similar to those possessed by polycarbonate can be used to prepare the slide holder of this invention.

When a cover slip must be removed from the major surface of a slide, suction can be used to remove the cover slip from the slide. Because of capillary attraction between the cover slip and the slide, it is possible that the cover slip will resist being removed from the major surface of the slide. The force generated by the suction will tend to promote unlocking of the latch 100 from the notch 120 in the side of the side wall 20 of the slide holder carrier 10 facing the latch 100. This result, i.e., unlocking, would be undesirable, particularly in an automated system. The retaining element 70, the projecting element 112, and the projecting element 114 assist in preventing suction from causing excessive upward movement of the slide from unlocking the latch 100 from the notch 120 in the side of the side wall 20 of the slide holder carrier 10 facing the latch 100. In one expected use of the present invention, a first cover slip is removed from the major surface of the slide, the specimen is then washed, a counter-stain is applied to the washed specimen, and then a second, new cover slip is dispensed over the specimen.

In certain embodiments of this invention, the slides must be able to contact a heater in order to carry out staining processes. For this reason, the slides must be able to float to ensure contact of the major surface of the slide with the heater. The design of the slide holder of this invention makes it possible for the slides to float in the slide holder so that a major surface of the slide can contact a heater, when required.

OPERATION

In order to insert a slide "S" into a slide holder 30, the latch 100 is unlocked, whereby the projecting element 118 is removed from the notch 120 in the side of the side wall 20 of the slide holder carrier 10 facing the latch 100 and the latch 100 is pivoted by means of the pins 126 and 128 to move the frame 32 of the slide holder 30 in a direction away from the second end wall 40. The latch 100 can be unlocked by lifting the overhanging portion 102a of the horizontal platform 102 of the latch 100 by a lifting mechanism (e.g., a thumb and finger of a human operator or an alternate mechanism, e.g., a robotic mechanism, an automated robotic mechanism). Such movement renders the top edges 34a, 36a of the side walls 34, 36, respectively, the horizontal platform 38c of the first end wall 38, and the horizontal platform 40c of the second end wall 40 of the frame 32 accessible to a loading mechanism (e.g., a thumb and a finger or a robotic mechanism), whereby the slide S can be placed on the frame 32 of the slide holder 30. A slide S is then placed onto the top edges 34a, 36a of the side walls 34, 36, respectively, in such a manner that the end $S_d$ of the slide S furthest from the second end wall 40 at which the latch 100 abuts the vertical portion 72 of the retaining element 70 on the horizontal platform 38c of the first end wall 38. The vertical portion 72 of the retaining element 70 prevents the slide S from sliding along the top edges 34a, 36a of the frame 32.

In order to lock the slide holder 30 to the slide holder carrier 10, the latch 100 is pivoted by means of the pins 126 and 128 to move the frame 32 of the slide holder 30 in a direction toward the second end wall 40 in such a manner that the projecting element 118 engages the notch 120 in the side of the side wall 20 of the slide holder carrier 10. The rotational movement of the latch 100 causes the projecting elements 112 and 114 to overlie the end $S_p$ of the slide S. In addition, the horizontal platform 102 of the latch 100 is restrained by the top of the end 20 of the slide holder carrier 10, so that the slide holder 30 does not rotate beyond the top of the end 20 of the slide holder carrier 10. Rotational movement of the latch 100 is effected by lowering the overhanging portion 102a of the horizontal platform 102 of the latch 100 by a lifting mechanism (e.g., a thumb and finger of a human operator, an alternate mechanism, e.g., a robotic mechanism, an automated robotic mechanism).

In the manner described above, other slides can be placed in the other slide holders 30.

In order to remove a slide S from a slide holder 30, the overhanging portion 102a of the horizontal platform 102 of the latch 100 is lifted so as to disengage the projecting element 118 from the notch 120 in the side of the side wall 20 of the slide holder carrier 10 facing the latch 100. The latch 100 is pivoted by means of the pins 126 and 128 to move the frame 32 of the slide holder 30 in a direction away from the second end wall 40, whereby the slide S can be removed from the top edges 34a, 34b of the side walls 34, 36, respectively, the horizontal platform 38c of the first end wall 38, and the horizontal platform 40c of the second end wall 40 of the frame 32 by a suitable removal mechanism, e.g., a finger and a thumb of a human operator or an alternate mechanism, e.g., a robotic mechanism, an automated robotic mechanism.

Thus, it can be seen that the slide S can easily be inserted into and removed from the slide holder 30.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A slide holder comprising a rectangular frame having two side walls facing each other, a first end wall facing a second end wall, the second end wall having a latch pivotally attached thereto, the latch capable of being pivoted in such a manner as to enable locking and unlocking of the slide holder in a slide holder carrier, wherein the latch comprises:
   (a) a first leg having a first end and a second end;
   (b) a second leg having a first end and a second end;
   (c) the first end of the first leg having an a first element projecting therefrom, the first projecting element capable of fitting into an opening in the side wall of the frame adjacent to the first end of the first leg;
   (d) the first end of the second leg having an a second element projecting therefrom, the second projecting element capable of fitting into an opening in the side wall of the frame adjacent to the first end of the second leg;
   (e) a third member disposed between the first leg and the second leg, the third member having a projecting element disposed between the first end of the first leg and the second end of the first leg and the first end of the second leg and the second end of the second leg, the projecting element projecting from a surface of the third member, whereby the projecting element of the third member is capable of engaging a notch in the slide holder carrier in order to lock the slide holder to the slide holder carrier;
   (f) a third projecting element on the first leg on the side opposite to that of the projecting element of component (e) to hold down a slide; and
   (g) a fourth projecting element on the second leg on the side opposite to that of the projecting element of component (e) to hold down a slide.

2. An assembly comprising at least one slide holder of claim 1, the assembly further comprising a slide holder carrier having a first end wall, a first side wall, a second end wall, a second side wall, and a shaft running from the first end wall of the slide holder carrier to the second end wall of the slide holder carrier, the at least one slide holder rotatably mounted on the shaft.

3. The assembly of claim 2, wherein a side wall of the slide holder carrier has a notch formed therein for mating with a projecting element on said latch to lock the slide holder to the slide holder carrier.

4. The assembly of claim 2, wherein the slide holder carrier further includes a plurality of ribs that divide the slide holder carrier into a plurality of cells, the ribs running from the first side wall to the second side wall.

* * * * *